United States Patent [19]

Knupp et al.

[11] Patent Number: 5,396,883
[45] Date of Patent: Mar. 14, 1995

[54] NEBULIZER VALVE ASSEMBLY FOR USE IN A VENTILATION CIRCUIT

[76] Inventors: Jacob E. Knupp, 114 Meadows Road S., Bourbonnais, Ill. 60914; Anthony D. Barber, 2295 W. Hickory, Kankakee, Ill. 60901

[21] Appl. No.: 62,229

[22] Filed: May 18, 1993

[51] Int. Cl.⁶ ............................................. A61M 11/00
[52] U.S. Cl. .......................... 128/200.14; 128/203.12; 128/205.11; 128/205.24
[58] Field of Search ...................... 128/200.14, 200.16, 128/203.12, 203.25, 205.11, 205.24, 204.25

[56] References Cited

U.S. PATENT DOCUMENTS

| | | | |
|---|---|---|---|
| 4,057,062 | 11/1977 | Lavigne | 128/912 |
| 4,267,832 | 5/1981 | Häkkinen | 128/205.24 |
| 4,281,652 | 8/1981 | Miller | 128/204.25 |
| 4,446,863 | 5/1984 | Rubin et al. | 128/912 |
| 4,637,384 | 1/1987 | Schroeder | 128/912 |
| 4,852,563 | 8/1989 | Gross | 128/202.27 |
| 4,951,661 | 8/1990 | Sladek | 128/202.27 |
| 5,027,809 | 7/1991 | Robinson | 128/912 |
| 5,062,419 | 11/1991 | Rider | 128/200.21 |

Primary Examiner—Kimberly L. Asher
Assistant Examiner—Aaron J. Lewis
Attorney, Agent, or Firm—Richard C. Litman

[57] ABSTRACT

A T-shaped valve for use in supporting a nebulizer cup in a ventilation circuit. The valve comprises an inner sheath and an outer sheath for supporting the inner sheath. Both the inner and outer sheaths have apertures which selectively align and misalign with one another. The inner sheath further includes an integral control knob which passes through an opening in the outer sheath. A displacement of the control knob shifts the inner sheath circumferentially relative to the outer sheath which, in turn, displaces the aperture in the inner sheath relative to the aperture in the outer sheath. When the aperture in the inner sheath is in communication with the aperture in the outer sheath, the circuit is open to permit fluid flow through the nebulizer cup and when the aperture in the inner sheath is not in communication with the aperture in the outer sheath, the circuit is closed to restrict fluid flow through the nebulizer cup and thus enable the removal of the nebulizer cup from the ventilation circuit. The valve is configured so as to prevent the aperture in the inner sheath from communicating with the opening in the outer sheath, to prevent axial displacement of the inner sleeve relative to the outer sleeve, and to provide a seal between the inner and outer sheaths.

6 Claims, 2 Drawing Sheets

NEBULIZER VALVE ASSEMBLY FOR USE IN A VENTILATION CIRCUIT

BACKGROUND OF THE INVENTION

1. Field of the Invention

The present invention relates to a pneumatic nebulizer valve assembly for use in ventilators or like apparatus and, more specifically, to a permanent in-line tee valve particularly suited to deliver medication to patients who are ventilator dependent.

2. Description of the Prior Art

A nebulizer is a pneumatically, or an electrically powered device that nebulizes or atomizes medications, at a particulate droplet size, to be delivered through an opening in the top of the nebulizer into a tee which is attached to the end of the ventilator circuit. The medication is then delivered through the ventilator tubing to the air passages of the patient. Conventionally, the tee is attached to the top of the nebulizer and placed in series within the ventilator circuit.

Presently, a patient on a ventilator may have to be completely taken off the ventilator for a brief time to initiate breathing treatment. This renders the circuit open, creating a situation that is potentially hazardous to both the patient and the staff. A control valve for restricting fluid flow through the nebulizer or for isolating the nebulizer from the rest of the ventilation circuit would not require the patient to be taken off the ventilator. One example of a control valve is shown in U.S. Pat. No. 4,281,652, issued Aug. 4, 1981 to Donald M. Miller. The control valve, referred to as a closable port, has a rebreathing bag connected thereto and is closable by a closure member. It is not clear how the closure member functions.

A valve apparatus is shown in U.S. Pat. No. 4,267,832, issued May 19, 1981 to Taisto Häkkinen, having an adjustment ring rotatably mounted over an exhalation valve. The exhalation valve has a front portion with an aperture or an exhalation port therein. The adjustment ring has an aperture provided therein which is movable over the front portion of the exhalation valve through the rotation of the adjustment ring. The adjustment ring is rotatable so that the aperture in the adjustment ring can be located in an overlapping relationship to the exhalation port located in the front portion of the exhalation valve. Unlike Häkkinen, applicants' instant invention is a T-shaped valve having an inner sheath supported by an outer sheath. The inner and outer sheaths each include an aperture. The apertures may be selectively aligned and misaligned through a rotational displacement of the inner sheath relative to the outer sheath to control fluid flow through the valve.

A tee valve assembly is described in U.S. Pat. No. 5,062,419, issued Nov. 5, 1991 to Donald L. Rider. The tee assembly includes a tee shaped based outer tube having a rotary valve control tube or inner tube therein. A bore in the tee shaped based outer tube includes a horizontal pipe and a shorter vertical pipe. The horizontal pipe includes a hole in communication with the vertical pipe. The inner tube includes a radial opening. The radial opening in the inner tube is alignable with the hole in the horizontal pipe by rotating the inner tube with respect to the horizontal pipe. A novel feature of applicants' invention is that the inner sheath remains substantially within the confines of the outer sheath. Another novel feature is that the outer sheath includes a circumferentially disposed opening passing therethrough and the inner sheath includes a control knob extending therefrom which passes through the opening in the outer sheath. The control knob is displaceable within the opening in the outer sheath to shift the inner sheath relative to the outer sheath. Neither of these features is shown in the Rider patent.

None of the above patents, taken either singly or in combination, is seen to describe the instant invention as claimed.

SUMMARY OF THE INVENTION

The present invention is a T-shaped valve for use in supporting a nebulizer cup in a ventilation circuit. The valve comprises an inner sheath and an outer sheath for supporting the inner sheath. The inner sheath has a control knob and an aperture, and the outer sheath has an opening and an aperture. The control knob is integral with the inner sheath and extends through the opening in the outer sheath. The aperture in the inner sheath selectively coaligns and misaligns with the aperture in the outer sheath. A displacement of the control knob shifts the inner sheath circumferentially relative to the outer sheath which, in turn, displaces the aperture in the inner sheath relative to the aperture in the outer sheath. When the aperture in the inner sheath is not in communication with the aperture in the outer sheath, the circuit is closed such as to restrict fluid flow through the nebulizer cup, thus enable the removal of the nebulizer cup from the ventilation circuit.

Accordingly, it is a principal object of the invention to provide a valve for use in supporting a nebulizer cup in a ventilation circuit wherein the valve includes an inner sheath supported by an outer sheath and wherein the inner and outer sheaths have apertures which selectively align and misalign with one another through the displacement of a control knob.

It is an object that an alignment of the apertures enable treatment to be given to a patient and discontinuation of treatment is accomplished through a misalignment of the apertures through a displacement of the control knob, whereby when the apertures are not aligned relative to one another, the ventilation circuit is closed to enable removal of the nebulizer cup.

It is an object that the control knob shift the inner sheath circumferentially relative to the outer sheath which, in turn, displaces the apertures relative to one another.

It is a further object that the outer sheath have an opening to permit the passage of the control knob therethrough wherein the opening is defined by an arcuate shaped slot circumferentially disposed within the peripheral wall of the outer sheath a predetermined angular distance from the aperture in the outer sheath.

Still another object is that the inner sheath be preferably fabricated of a pliable material to permit the same to be distorted and inserted into the outer sheath, whereby the inner sheath may be inserted within the outer sheath to a point where the control knob aligns with and passes through the opening and thereafter the inner sheath returns to its initial shape, thus forming a peripheral seal between the inner sheath and the outer sheath.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
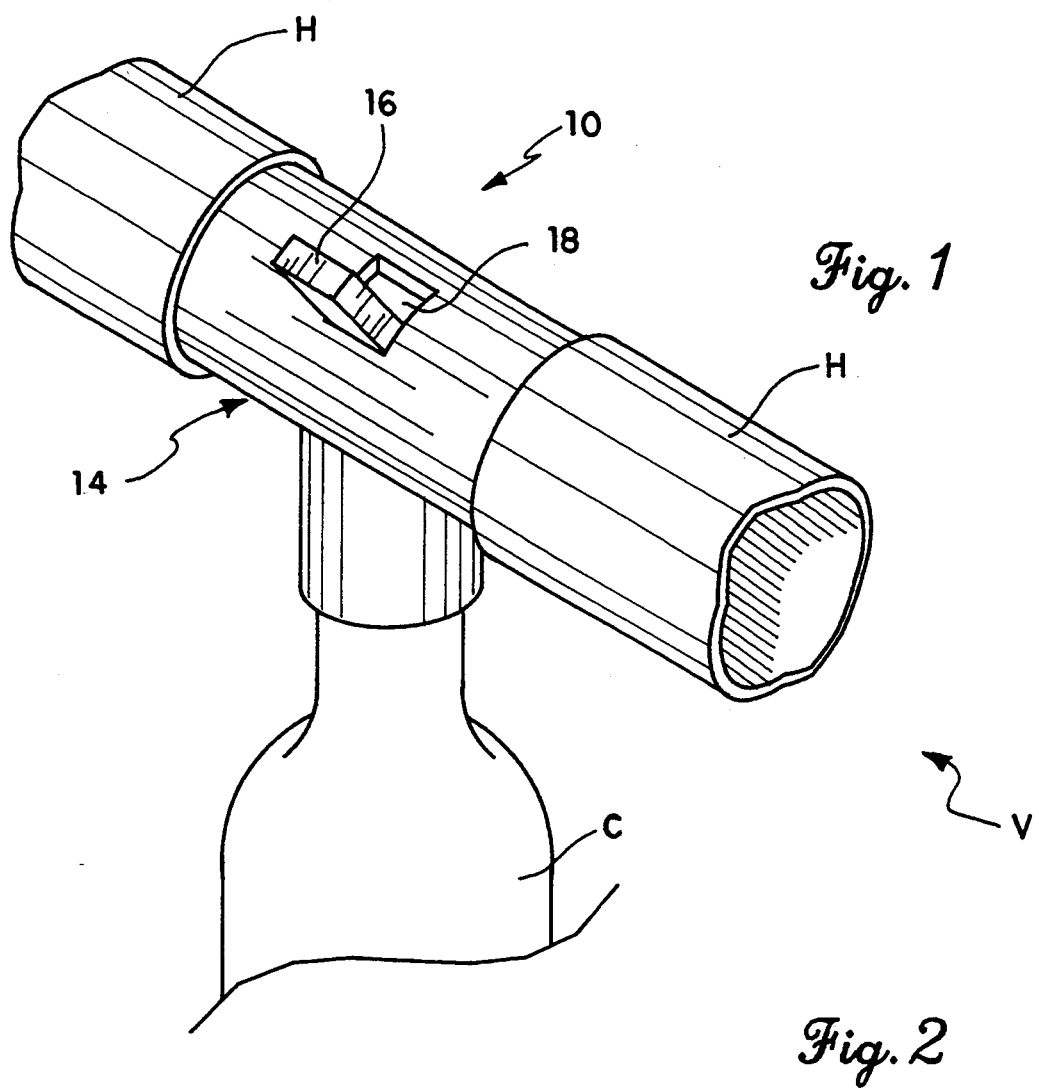
FIG. 1 is a perspective view of a tee valve assembly according to the present invention.

The present invention, as shown in FIG. 1, is a T-shaped valve 10 for use in supporting a nebulizer cup C in a ventilation circuit V. The valve 10 has two ends, each being of substantial length to accommodate hoses H of the ventilation circuit V. The valve 10 comprises an inner sheath 12, shown more clearly in FIGS. 3 and 4, supported by an outer sheath 14. The inner sheath 12 has a control knob 16 and the outer sheath 14 has an opening 18. The control knob 16 is integral with the inner sheath 12 and extends through the opening 18 in the outer sheath 14. The displacement of the control knob 16 shifts the inner sheath 12 circumferentially relative to the outer sheath 14 to selectively open and close the valve 10. With the valve 10 in the closed position, the ventilation circuit V is closed to enable removal of the nebulizer cup C.

Figure 2:
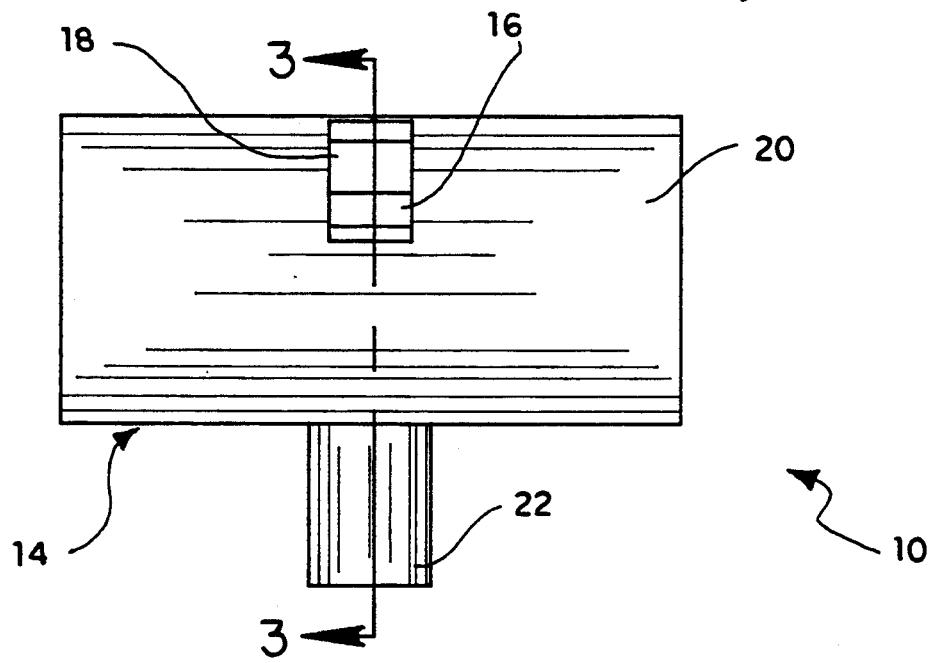
FIG. 2 is a front elevational view of the valve assembly shown in FIG. 1

Now referring to FIG. 2, the outer sheath 14 includes a first tube 20 and a second tube 22 somewhat smaller than the first tube 20. The second tube 22 is disposed perpendicularly relative to the first tube 20 and is integral with the first tube 20. The opening 18 in the first tube 20 is defined by an arcuate shaped slot circumferentially disposed within the outer sheath 14 a predetermined angular distance from the second tube 22. The arcuate slot 18, shown more particularly in FIG. 1, is bounded by four walls intersecting substantially at right angles relative to one another, the four walls being formed through the peripheral wall of the first tube 20. The control knob 16 passes through the opening 18 and has a circumferential displacement limited between opposing longitudinally extending walls defining the circumferential boundaries of the arcuate slot. Opposing circumferentially extending walls are spaced apart such that the control knob 16 spans longitudinally therebetween, restricting the axial or longitudinal movement of the inner sleeve relative to the outer sleeve.

The inner sheath 12 with the control knob 16 is preferably fabricated of resilient or a pliable memory retentive material which permits the same to be temporarily deformed and inserted into the outer sheath 14. The inner sheath 12 is inserted into the outer sheath 14 to the point where the control knob 16 aligns with and passes through the opening 18. Thereafter, the inner sheath 12 returns to its initial or normal shape, thus forming a peripheral seal between the outer peripheral surface of the inner sheath 12 and the inner peripheral surface of the outer sheath 14.

Figure 3:
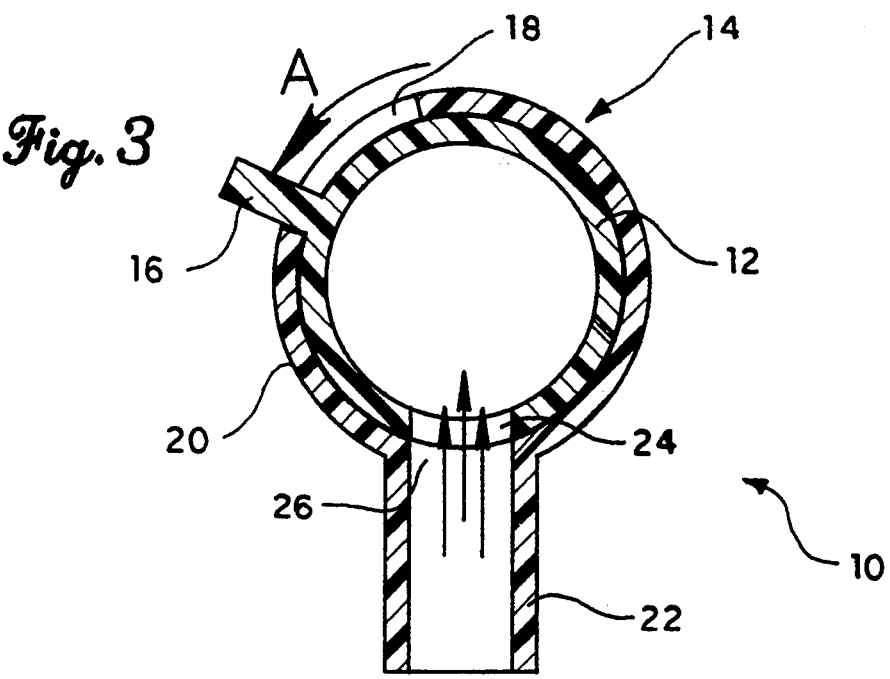
FIG. 3 is a cross-sectional view of the valve drawn along lines 3—3 of FIG. 2.

In FIG. 3, the valve 10 is shown in an open position. The inner sheath 12 has an aperture 24 therein disposed a predetermined angular distance form the control knob 16. The first tube 20 of the outer sheath 14 has an aperture 26 passing therethrough which communicates with the second tube 22. Upon displacement of the control knob 16 in a direction A, the aperture 26 coaligns with the aperture 24 in the inner sheath 12. An alignment of the apertures 24, 26 permits fluid flow F from the nebulizer cup C (shown in FIG. 1) to enable treatment to be given to the patient (not shown). It is clearly seen that the control knob 16 is integral with the inner sheath 12 and extends through the opening 18 in the outer sheath 14. The control knob 16 is shown to extend radially from the inner sleeve 12 and the aperture 24 is shown to extend radially through the inner sheath 12.

Figure 4:
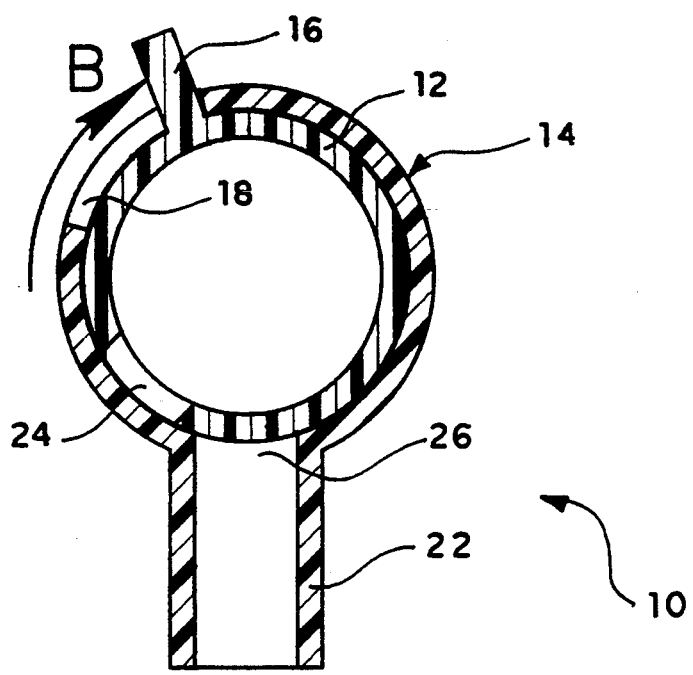
FIG. 4 is a cross-sectional view similar to FIG. 3 but showing the valve in a closed position.

Now referring to FIG. 4, the valve 10 is shown in a closed position. Discontinuation of treatment is accomplished through a displacement of the control knob 16 in the direction B through the opening 18 in the outer sheath 14. The displacement of the control knob 16 rotatably shifts the inner sheath 12 circumferentially relative to the outer sheath 14 which, in turn, displaces the aperture 24 in the inner sheath 12 relative to the aperture 26 in the outer sheath 14. When the aperture 24 in the inner sheath 12 is not in communication with the aperture 26 in the outer sheath 14, the ventilation circuit V (shown in FIG. 1) is closed with respect to fluid flow through the second tube 22 of the outer sheath 14 through the seal formed between the outer peripheral surface of the inner sheath 12 and the inner peripheral surface of the outer sleeve 14 to enable the removal of the nebulizer cup C (shown in FIG. 1). Note that the dimensions and the configuration of the valve 10 and more particularly, of the opening 18 in the outer sheath 14 are such that the opening 18 in the outer sheath 14 is not permitted to communicate with the aperture 24 in the inner sheath 12, thus ensuring that the valve 10 remains sealed from air from outside of the ventilation circuit V (shown in FIG. 1).

It is to be understood that the present invention is not limited to the sole embodiment described above, but encompasses any and all embodiments within the scope of the following claims.

We claim:

1. A ventilation circuit having a valve and a nebulizer cup, said valve comprising:

an inner sheath fabricated of a pliable, memory retentive material, and an outer sheath;

said inner sheath including an aperture passing therethrough and a control knob integral therewith; and said outer sheath including a first tube and a second tube;

said first tube having a peripheral wall, an opening in said peripheral wall, and an aperture in said peripheral wall at a predetermined angular distance from said opening;

said second tube having a first end in communication with said aperture in said first tube, and a second end removably connected to and in communication with said nebulizer cup; wherein said inner sheath being of a predetermined size, the inner sheath being deformed responsive to telescopic insertion into said outer sheath to a position where said control knob aligns with and extends through said opening in said outer sheath, forming a peripheral seal between the inner and outer sheath;

said control knob being rotated to cause said inner sheath to move circumferentially relative to said outer sheath and selectively allowing communication between the nebulizer cup and a patient connected to the ventilation circuit.

2. The valve according to claim 1, wherein said first tube includes two ends for attachment to a hose of the ventilation circuit.

3. The valve according to claim 1, wherein said opening is defined by an arcuate shaped slot circumferentially disposed within said outer sheath.

4. The valve according to claim 1, further including means to limit a circumferential displacement of said control knob.

5. The valve according to claim 1, further including means to limit axial displacement of said control knob.

6. The valve according to claim 1, wherein said second tube is substantially perpendicular to said first tube so as to form a T-configuration.

* * * * *